United States Patent [19]

Ward

[11] 4,342,761
[45] Aug. 3, 1982

[54] PIPERIDINE DERIVATIVES

[75] Inventor: Terence J. Ward, Slough, England

[73] Assignee: John Wyeth & Brother Limited, Maidenhead, England

[21] Appl. No.: 198,414

[22] Filed: Oct. 20, 1980

[30] Foreign Application Priority Data

Nov. 1, 1979 [GB] United Kingdom ............... 7937811

[51] Int. Cl.³ .................. A61K 31/445; C07D 419/14
[52] U.S. Cl. .................................. 424/246; 546/198; 546/200; 546/201; 544/49; 424/267
[58] Field of Search ................. 544/49; 546/198, 201; 424/246, 267

[56] References Cited

U.S. PATENT DOCUMENTS

| | | | |
|---|---|---|---|
| 4,045,566 | 8/1977 | Archibold et al. | 546/201 |
| 4,144,344 | 3/1979 | Eichenberger et al. | 546/201 |
| 4,224,333 | 9/1980 | Clemence et al. | 546/201 |
| 4,281,132 | 7/1981 | Ward | 546/214 |

Primary Examiner—Robert T. Bond
Attorney, Agent, or Firm—Richard K. Jackson

[57] ABSTRACT

Compounds having the formula

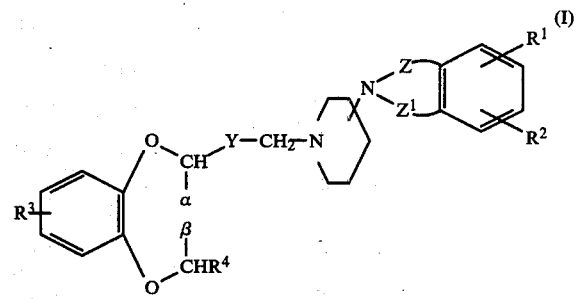

wherein Y represents —CHOH— or

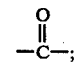

Z and $Z^1$ independently represent

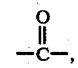

—$SO_2$—, —$COCH_2$—, or —$CO(CH_2)_2$—; Z may also represent —$CH_2$—, —$(CH_2)_2$—, —CHMe—, or —C$Me_2$—; $R^1$ and $R^2$ independently represent hydrogen or substituents selected from halogen, lower-alkoxy, nitro, amino, lower alkylamino, trifluoromethyl, hydroxy, aryl lower alkoxy and lower alkyl; or $R^1$ and $R^2$ when adjacent together with the carbon atoms to which they are attached form a six membered carbocyclic ring; $R^3$ represents hydrogen, halogen, lower alkyl or lower alkoxy, $R^4$ represents lower alkyl or hydrogen; α and β each represent hydrogen or a direct bond between the carbon atoms to which they are attached, and acid addition quaternary ammonium salts thereof, are disclosed which possess antihypertensive activity.

8 Claims, No Drawings

PIPERIDINE DERIVATIVES

This invention relates to piperidine derivatives having pharmaceutical activity, to processes for their preparation, to pharmaceutical compositions containing them, and to intermediates useful in their preparation.

This invention provides new compounds having the formula

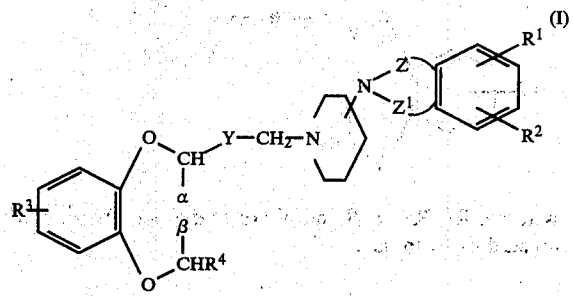

wherein Y represents —CHOH— or

Z and Z¹ independently represent

—SO₂—, —COCH₂—, or —CO(CH₂)₂—; Z may also represent —CH₂—, —(CH₂)₂—, —CHMe—, or —CMe₂—; $R^1$ and $R^2$ independently represent hydrogen or substituents selected from halogen, lower-alkoxy, nitro, amino, lower alkylamino, trifluoromethyl, hydroxy, aryl lower alkoxy and lower alkyl; or $R^1$ and $R^2$ when adjacent together with the carbon atoms to which they are attached form a six membered carbocyclic ring; $R^3$ represents hydrogen, halogen, lower alkyl or lower alkoxy, $R^4$ represents lower alkyl or hydrogen; α and β each represent hydrogen or a direct bond between the carbon atoms to which they are attached; and acid addition quaternary ammonium salts thereof. The term "aryl" means a carbocyclic aromatic ring.

The term "lower" as used herein in connection with such groups as "alkyl" and "alkylene" denotes that the group contains up to 6 carbon atoms, preferably not more than 4 carbon atoms.

Examples of lower alkyl groups for $R^1$, $R^2$, $R^3$ and $R^4$ are methyl, ethyl, n-propyl, i-propyl, n-butyl, n-pentyl and n-hexyl. Preferred lower alkyl groups are methyl and ethyl.

Examples of $R^1$, $R^2$ or $R^3$ when halogen are fluorine, chlorine or bromine.

Examples of lower alkoxy groups for $R^1$, $R^2$ and $R^3$ are methoxy, ethoxy, n-propoxy, isopropoxy and n-butoxy.

Preferred lower alkoxy groups are methoxy and ethoxy. When aryl lower alkoxy, $R^1$ or $R^2$ is preferably benzyloxy. Preferably Z and Z¹ are both —CO— or Z is —CO— and Z¹ is —SO₂—. Preferably the piperidine ring is substituted in the 4-position. Preferably $R^{1-4}$ are hydrogen. Preferably Y is —CHOH—.

Examples of acid addition salts are those formed from inorganic and organic acids and in particular pharmaceutically acceptable acid addition salts such as the hydrochloride, hydrobromide, hydroiodide, sulphate, nitrate, phosphate, sulphonate (such as the methanesulphonate and p-toluenesulphonate), acetate, maleate, citrate, fumarate, tartrate, malonate and formate.

Examples of quaternary ammonium compounds are those formed with alkyl and aralkyl halides, particularly methyl and ethyl halides such as ethyl bromide and methyl iodide, and benzyl halides such as benzyl chloride.

It will be apparent to those skilled in the art that the compounds of formula I may possess one, and sometimes two asymmetric centres and hence optical isomers and sometimes diastereoisomers are possible. All such optically active forms and mixtures thereof, are intended to be included within the scope of this invention. More particularly when Y represents the group —CHOH— in formula I above and α and β are a direct bond then two asymmetric centres are present and therefore such a compound can exist in one of four optically active forms, i.e. two pairs of enantiomers-one pair of enantiomers being the diastereoisomers of the other pair. Such diastereoisomeric forms are termed threo and erythro and have the relative configurations shown below:

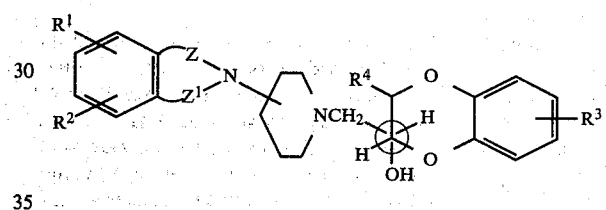

threo (RR/SS)

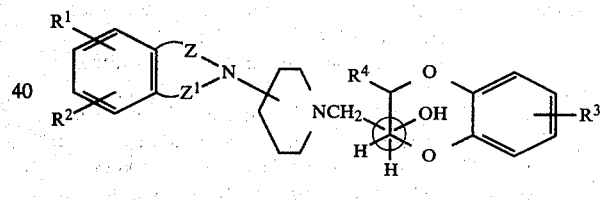

erythro (RS/SR)

Separation of diastereoisomers and enantiomers may be effected by standard techniques known in the art.

Compounds of formula I, wherein Y is CHOH and α and β are a direct bond, having the erythro configuration are particularly preferred.

Preferred compounds of the invention are erythro 2-([2-(1,4-benzodioxan-2-yl)-2-hydroxyethyl]piperid-4-yl)-1,2-benzoisothiazolin-3-one-1,1-dioxide and erythro 2-([2-(1,4-benzodioxan-2-yl)-2-hydroxyethyl]piperid-4-yl)-1H-isoindol-1,3-(2H)-dione.

The compounds of this invention possess pharmaceutical activity and some are intermediates for other compounds of this invention. More particularly, compounds of this invention have been found to possess action on the cardiovascular system such as antihypertensive activity, adrenergic blocking activity. Compounds possessing such activities are useful in the treatment or prophylaxis of coronary artery disorders.

Antihypertensive activity was determined by the following test:

Female rats are rendered hypertensive by implanting subcutaneously two wax pellets (30 mg) containing desoxycorticosterone acetate (15 mg) followed immediately by uninephrectomy. The drinking water is replaced by normal saline ad lib for 4 weeks. Blood pressure stabilises at a hypertensive level after 6 weeks. Systolic pressure is measured indirectly before dosing with a test compound using an E and M pneumatic pulse transducer and a Devices MX2 recorder. Groups of 4 rats are dosed orally with suspensions or solutions of the test compound in 0.5% hydroxypropylmethylcallulose 0.9% saline vehicle. Blood pressures are recorded again at 2, 6 and 24 hours and the results, expressed as a percentage of the pre-dose values compared with those of a similar group of rats receiving vehicle alone.

Representative of the compounds of formula I is erythro 2-([2-(1,4-benzodioxan-2-yl)-2-hydroxyethyl]-piperid-4-yl)-1,2-benzoisothiazolin-3-one-1,1-dioxide hydrochloride, which showed marked antihypertensive activity at a dose level of 50 mpk in the above mentioned test, producing a 44% and 36.5% decrease in systolic blood pressure at a time period of 2 hours and 6 hours respectively after dosing. At a dose level of 10 mpk this compound gave a 25% decrease in systolic blood pressure 2 hours after dosing. The compound erythro 2-([2-(1,4-benzodioxan-2-yl)-2-hydroxyethyl]-piperid-4-yl)-1H-isoindol-1,3-(2H)-dione hydrochloride at 50 mpk in the same test produced a 40% and 32% decrease in blood pressure 2 and 6 hours respectively after dosing.

Adrenergic blocking activity on $\alpha$ and $\beta$ receptors was evidenced by standard tests on isolated animal tissue; The representative compound erythro 2-([2-(1,4-benzodioxan-2-yl)-2-hydroxyethyl]piperid-4-yl)-1,2-benzoisothiazolin-3-one-1,1-dioxide hydrochloride was found to possess an $\alpha$-adrenoceptor blockade $pA_2$ value of 9.2 when tested on rat perfused mesenteric vasculature. This compound also showed an ability to block isoprenaline-induced positive chronotropic responses of guinea pig isolated atria (at $10^{-5}$ and $10^{-6}$M) without affecting those to aminophylline; thereby indicating $\beta$-adrenoceptor blocking activity.

Compounds of formula I wherein Y represents —CO— are useful for preparing compounds of formula I wherein Y represents —CHOH— and vice versa.

A first process for preparing a compound of formula I comprises reacting a compound of formula II

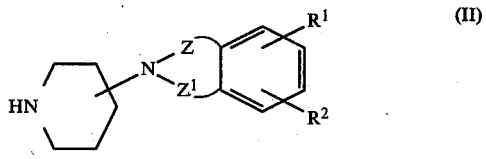

wherein $R^1$, $R^2$, Z and $Z^1$ are as defined in connection with formula I, with a compound of formula III

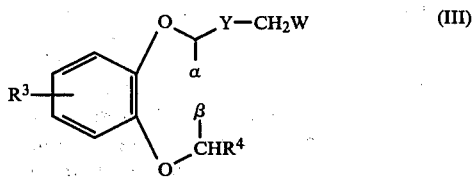

wherein $R^3$, $R^4$, $\alpha$, $\beta$ and Y are as defined above and W represents a leaving group, such as halogen (e.g. chlorine, bromine or iodine), an organic sulphonyloxy radical (e.g. tosyloxy, mesyloxy). Where the leaving group is a halogen or an organic sulphonyloxy redical the reaction is preferably carried out in the presence of base, e.g. potassium carbonate, triethylamine.

A second general process for preparing compounds of formula I (wherein Z is —CO—, —COCH$_2$—, —SO$_2$— or —CO(CH$_2$)$_2$—) comprises reacting a compound of formula IV

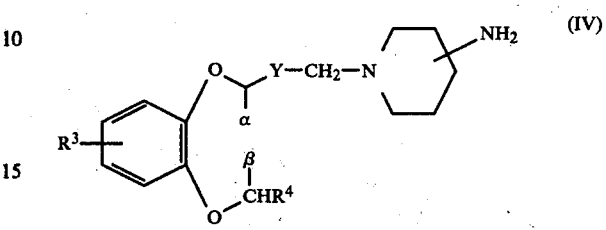

wherein $R^3$, $R^4$, $\alpha$, $\beta$ and Y are as defined above, with an acid of formula

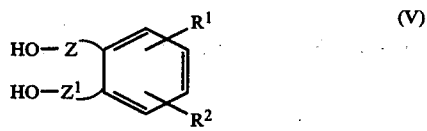

or a reactive derivative thereof, wherein $Z^1$, $R^1$ and $R^2$ are as hereinbefore defined and Z is as defined immediately above. Examples of reactive derivatives of the acid of formula (V) are the di- acid halide (e.g. chloride) and the acid anhydride. This reaction may be brought to completion by employing a dehydrating agent (e.g. acetic anhydride). Other reactive derivatives include alkoxycarbonylimides. When Y=CH(OH) protection is required.

A further process for preparing a compound of formula I comprises reducing a compound of formula VI or VII

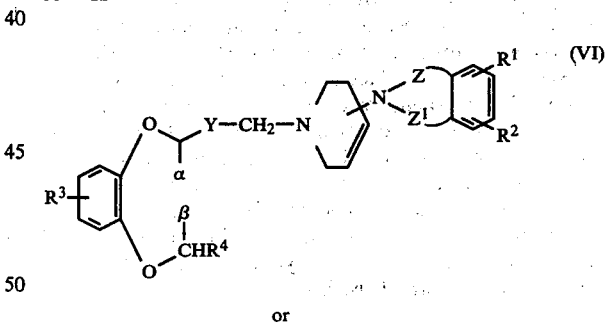

or

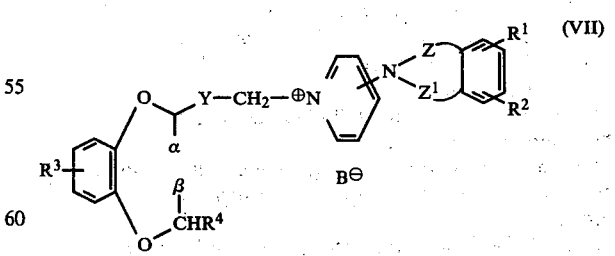

wherein $R^1$, $R^2$, $R^3$, $R^4$, $\alpha$, $\beta$, Y, Z and $Z^1$ are as hereinbefore defined and $B^{\ominus}$ represents an anion, e.g. a halide ion; for example by catalytic hydrogenation, e.g. in the presence of Raney nickel or platinum catalyst. The reduction may also be effected by a process described and claimed in our U.K. Pat. No. 1,542,137. Such a reduction process employs an alkali metal borohydride in a secondary alkanol having 3-5 carbon atoms, e.g. isopropanol.

Yet a further process for preparing a compound of formula I comprises reacting a compound of formula VIII

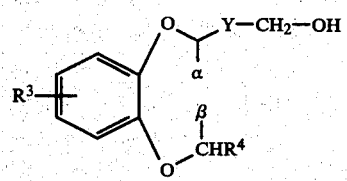

wherein $\alpha$, $\beta$, Y, $R^3$ and $R^4$ are as hereinbefore defined with a compound of formula II, in the presence of a catalyst, e.g. Raney nickel. When Y=CH(OH) protection is required.

Compounds of formula I wherein the piperidine ring is substituted in the 4-position may also be prepared by a process which comprises reacting a compound of formula

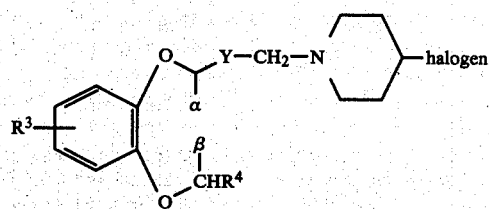

with an alkali metal salt of a compound of formula

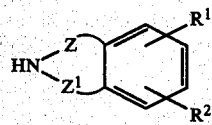

in which formulae $\alpha$, $\beta$, Y, Z, $Z^1$, $R^1$, $R^2$, $R^3$ and $R^4$ are as hereinbefore defined.

Examples of halogen in the compound of formula IX are chlorine and bromine. Examples of alkali metal salts of the compound of formula X are the potassium and sodium salts.

The compounds of formula (I) wherein Y is —CHOH— are also obtained by reacting a compound of formula

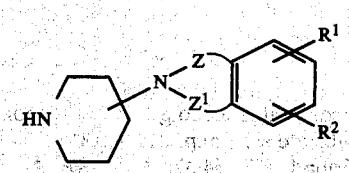

with an epoxide of formula

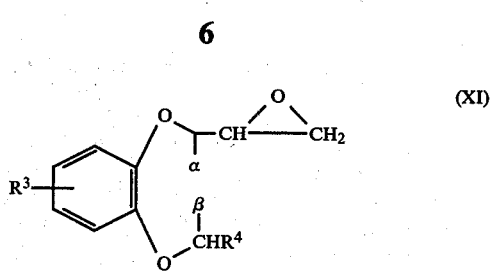

in a suitable organic solvent such as an aromatic hydrocarbon for example, benzene, toluene, xylene and the like; a halogenated hydrocarbon such as chloroform and methylene chloride; or a lower alkanol, such as, for example, methanol, ethanol, 2-propanol and the like and preferably in a mixture of an aromatic hydrocarbon and a lower alkanol.

Once a compound of formula I wherein Y is —CO— has been prepared then such a compound may be reduced to give other compounds of formula I wherein Y is —CHOH—. For example reduction may be effected with a hydride transfer agent such as an alkali metal borohydride, e.g. sodium borohydride, and sodium tri-t-butoxyborohydride. Other methods applicable to the reduction of a ketone to a secondary alcohol are known in the literature; see for example "Compendium of Organic Synthetic Methods" Ian T. Harrison, Suyen Harrison, published by Wiley Interscience, Volume I, 1971.

Once a compound of formula I wherein Y is —CHOH— has been prepared then such a compound may be oxidised to give other compounds of formula I wherein Y is —CO—. For example, chromic acid oxidation may be used to effect the above mentioned conversion. Other methods for oxidising secondary alcohols to ketones are known in the literature, see for example, the above mentioned textbook of Harrison and Harrison.

Separation of diastereoisomers and resolution of enantiomers may be effected by standard techniques known in the art after any of the above mentioned processes where mixtures of isomers or racemic starting materials are employed. For example diastereoisomers can generally be separated by techniques such as fractional crystallisation or chromatography.

Alternatively it will be apparent to those skilled in the art that if it is desired to prepare a final product having a specific stereochemistry then it is possible in some instances to employ a starting material already having the desired stereochemistry. Such routes to erythro compounds of formula I are preferred. For example erythro compounds of formula (III) as defined above may be reacted with compounds of formula (II) to give corresponding erythro compounds of formula I.

Once a compound of formula I has been prepared then that compound may be converted in known manner to other compounds of formula I. When $R^3$ is lower alkoxy or aryl lower alkoxy dealkylation produces a corresponding compound of formula I wherein $R^3$ is hydroxy. When any of $R^1$, $R^2$ and $R^3$ is nitro then reduction (e.g. catalytic hydrogenation) can be used to convert the nitro group to an amino group.

Compounds of formula I wherein Z is —CH$_2$— or —(CH$_2$)$_2$— may be prepared by reducing, e.g. using zinc dust in glacial acetic acid, a corresponding compound of formula I wherein Z is —CO— or —COCH$_2$—.

The aforementioned processes may also include the step of conversion of an acid addition salt into the free base form or vice versa. Quaternisation of the tertiary nitrogen of the piperidine ring may be included as an optional after step, e.g. using alkyl or aryl lower alkyl halides, e.g. methyl iodide, benzyl chloride.

Starting materials used in the above mentioned processes are known compounds or may be prepared by analogous processes. For example, a compound of formula II may be prepared by reducing the corresponding compound of formula XII

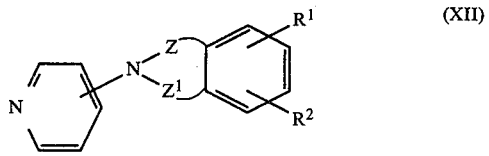

(XII)

using for example catalytic hydrogenation. Compounds of formula XII may be prepared by reacting a halopyridine with an alkali metal salt of compound of formula X, or by reacting a 3 or 4-aminopyridine with a di-acid or reactive derivative of formula V.

Compounds of formula VII may be prepared by reacting a compound of formula III wherein W is halogen, especially bromine, with a compound of formula XII.

Compounds of formula VI may be prepared by reducing, e.g. using sodium borohydride in methanol, a compound of formula VII.

Compounds of formula II wherein Z is —CO— or COCH$_2$— may be reduced, e.g. using zinc dust in glacial acetic acid, to give corresponding compounds of formula II wherein Z is —CH$_2$— or (CH$_2$)$_2$—.

Starting materials of formula IV may be prepared by methods disclosed in our U.K. Pat. No. 1,345,872.

If necessary, in any of the reactions herein described, reactive substituent groups may be blocked during a reaction and released at a later stage. For example when Y is CHOH it may be protected by groups such as benzyl or acyl which are easily removable by known methods.

This invention also includes pharmaceutical compositions containing as active ingredient an active compound of formula I as defined above. The active compound may be finely comminuted if desired. In addition to the active ingredient, the compositions also contain a pharmaceutically acceptable carrier. Any suitable carrier known in the art can be used to prepare the pharmaceutical compositions. In such a compositions, the carrier may be a solid, liquid or mixture of a solid and a liquid.

Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient.

Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxy-methyl cellulose solution, or in a suitable oil, for instance arachis oil. Liquid pharmaceutical compositions which are sterile solutions or suspensions can be utilized by intramuscular, intraperitoneal or subcutaneous injection. In many instances, a compound is orally active and can be administered orally either in liquid or solid composition form.

Preferably the pharmaceutical composition is in unit dosage form. In such form, the composition is subdivided in unit doses containing appropriate quantities of the active ingredients; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg or less to 500 or more, according to the particular need and the activity of the active ingredient. The invention also includes the compounds in the absence of carrier where the compounds are in unit dosage form.

The following Examples illustrate the invention:

EXAMPLE 1

Erythro 2-([2-(1,4-benzodioxan-2-yl)-2-hydroxyethyl]piperid-4-yl)-1,2-benzoisothiazolin-3-one-1,1-dioxide Erythro 1-(1,4-Benzodioxan-2-yl)-2-bromoethanol (1.29 g, 0.005 m), 2-(piperid-4-yl)-1,2-benzisothiazolin-3-one-1,1-dioxide hydrochloride (1.44 g, 0.005 m) and triethylamine (4 cm$^3$) were refluxed for 24 hours in ethanol (50 cm$^3$). The solution was cooled, the solvent evaporated and the residue treated with water. The product was extracted with chloroform, washed with water and dried (MgSO$_4$). Evaporation gave a gum which was dissolved in isopropyl alcohol. The crystallised solid was collected by filtration, dissolved in ethanol and treated with ethanolic HCl. Ether was added and the resulting precipitate filtered off and recrystallised from isopropyl alcohol to give the title compound as the hydrochloride salt, m.p. 216°–218° C.

Analysis: Found: C, 54.47; H, 5.10; N, 5.93%. C$_{22}$H$_{24}$N$_2$O$_6$S.HCl requires: C, 54.94; H, 5.24; N, 5.82%.

EXAMPLE 2

Erythro 2-([2-(1,4-Benzodioxan-2-yl)-2-hydroxyethyl]piperid-4-yl)-1H-isoindole-1,3-(2H)-dione Erythro, 1-(1,4-benzodioxan-2-yl)-2-bromoethanol (1.29 g, 0.005 m) and 2-(piperid-4-yl)-1H-isoindole-1,3-(2H)dione hydrochloride (1.33 g, 0.005 cm³) in ethanol (75 cm³) with triethylamine (3.03 g, 0.03 cm³) were refluxed for 18 hours. The solution was cooled and the solvent evaporated. the residue was dissolved in chloroform and then washed twice with water, dried (MgSO₄) and evaporated. The residue was dissolved in isopropyl alcohol and acidified with ethanolic HCl. The crystallised material was filtered to give the title compound as the hydrochloride salt m.p. 235°–237° C.

Analysis: Found: C, 61.95; H, 5.76; N, 6.09%. $C_{23}H_{24}N_2O_5 \cdot HCl$ requires: C, 62.09; H, 5.66; N, 6.30%.

EXAMPLE 3

Repeating the procedure of Example 1 the following compounds of formula I may be prepared according to the reaction scheme:

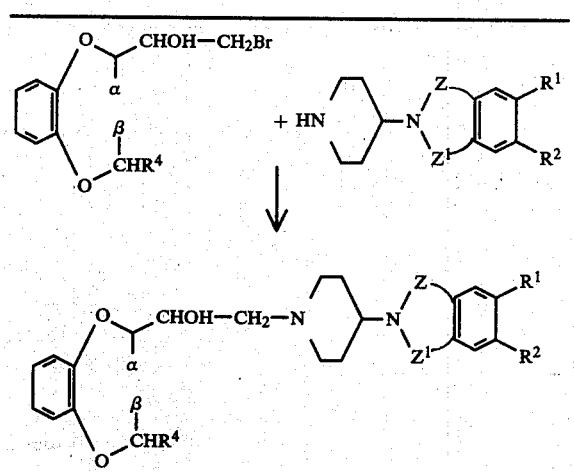

| | α/β | R¹ | R² | R⁴ | Z | Z¹ |
|---|---|---|---|---|---|---|
| (a) | H | H | H | H | —CO— | —SO₂— |
| (b) | H | H | H | H | —CO— | —CO— |
| (c) | single bond* | H | H | H | —SO₂— | —SO₂— |
| (d) | single bond* | H | H | CH₃ | —CO— | —SO₂— |
| (e) | single bond* | CH₃ | H | H | —CO— | —SO₂— |
| (f) | single bond* | Cl | H | H | —CO— | —SO₂— |
| (g) | single bond* | H | Br | H | —COCH₂— | —SO₂— |
| (h) | single bond* | Cl | Cl | H | —CO— | —SO₂— |
| (i) | single bond* | NO₂ | H | H | —CO— | —SO₂— |
| (j) | single bond* | CH₃O | H | H | —CO— | —SO₂— |
| (k) | single bond* | CF₃ | H | H | —CO— | —SO₂— |

*Configuration of asymmetric centers = erythro.

I claim:

1. A compound of the formula:

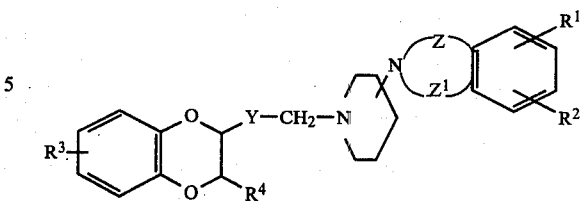

and acid addition and quaternary ammonium salts thereof, wherein Y represents —CHOH— or —CO—; Z and Z¹ represent, independently, —CO—, —SO₂— or —COCH₂—; R¹ and R² independently represent hydrogen, halogen, lower alkyl, lower alkoxy, nitro or trifluoromethyl; R³ represents hydrogen, halogen, lower alkyl or lower alkoxy and R⁴ represents lower alkyl or hydrogen.

2. A compound as claimed in claim 1 wherein Y is —CHOH—.

3. A compound of the formula:

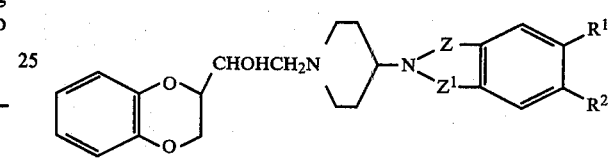

and acid addition and quaternary ammonium salts thereof wherein Z and Z¹ independently represent —CO—, —SO₂— or —COCH₂— and R¹ and R² independently represent hydrogen, halogen, lower alkyl, lower alkoxy, nitro or trifluoromethyl.

4. A compound as claimed in claim 3 in which Z¹ is —SO₂—.

5. A compound as claimed in claim 4 which is erythro 2-([2-(1,4-benzodioxan-2-yl)-2-hydroxy-ethyl]-piperid-4-yl)-1,2-benzisothiazolin-3-one-1,1-dioxide or a pharmaceutically acceptable acid addition or quaternary ammonium salt thereof.

6. A compound as claimed in claim 3 which is erythro-2-([2-(1,4-benzodioxan-2-yl)-2-hydroxyethyl]piperid-4-yl)-1H-isoindole-1,3-(2H)-dione, or a pharmaceutically acceptable acid addition or quaternary ammonium salt thereof.

7. An antihypertensive pharmaceutical composition comprising a therapeutically effective amount of a compound as claimed in claim 1 or a pharmaceutically acceptable acid addition or quaternary ammonium salt thereof, together with a pharmaceutically acceptable carrier.

8. A method of treating an animal afflicted with a disease or disorder requiring action on the cardiovascular system which comprises administering to said animal an effective amount of a compound as claimed in claim 1 or a pharmaceutically acceptable acid addition or quaternary ammonium salt thereof.

* * * * *